United States Patent
Ham et al.

(10) Patent No.: US 9,895,409 B2
(45) Date of Patent: Feb. 20, 2018

(54) REMEDY FOR GASTRITIS AND GASTRIC ULCER

(71) Applicant: Mokpo National University Industry-Academia Cooperation Group, Jeollanam-do (KR)

(72) Inventors: Kyung Sik Ham, Gwangju (KR); Jeong Yong Cho, Gwangju (KR); Tian-cheng Gao, Jeollanam-do (KR); Ling-yun Feng, Jeollanam-do (KR); Zhang-jun Hwang, Jeollanam-do (KR)

(73) Assignee: MOKPO NATIONAL UNIVERSITY INDUSTRY-ACADEMIA COOPERATION GROUP, Jeollanam-Do (KR)

( * ) Notice: Subject to any disclaimer, the term of this patent is extended or adjusted under 35 U.S.C. 154(b) by 0 days.

(21) Appl. No.: 15/404,097

(22) Filed: Jan. 11, 2017

(65) Prior Publication Data

US 2017/0119838 A1 May 4, 2017

Related U.S. Application Data

(63) Continuation of application No. 14/649,753, filed as application No. PCT/KR2011/009614 on Dec. 14, 2011, now abandoned.

(30) Foreign Application Priority Data

May 27, 2011 (KR) .......................... 10-2011-0050650

(51) Int. Cl.
*A61K 36/899* (2006.01)
*A61K 33/04* (2006.01)

(52) U.S. Cl.
CPC ............ *A61K 36/899* (2013.01); *A61K 33/04* (2013.01)

(58) Field of Classification Search
None
See application file for complete search history.

(56) References Cited

FOREIGN PATENT DOCUMENTS

| KR | 10-1996-0021033 | | | 7/1996 |
|----|-----------------|---|---|--------|
| KR | 10-2005-0088812 | | | 9/2005 |
| KR | 10-2010-0003068 | | | 1/2010 |
| KR | 10-2010003068   | A | * | 1/2010 |
| KR | 2010-048866     | A | * | 5/2010 |
| KR | 10-2011-0000805 | | | 1/2011 |
| KR | 10-2011-0000805 | A | * | 1/2011 |

OTHER PUBLICATIONS

Shin, et al. (2003) "Anti-inflammatory activity of Korean folk medicine purple bamboo salt." *Immunopharmacol Immunotoxicol.*, 25(3):377-384.
Shin, et al. (2004) "Biological Activity of Bamboo Salt." *Food Industry and Nutrition*, 9(1):36-45 (Abstract Only).
http://www.ozoneapplications.com/info/sulfur.htm—accessed Oct. 2015.
International Search Report (ISR) dated Jun. 21, 2012 in PCT/KR2011/009614 with English Translation.

* cited by examiner

*Primary Examiner* — Susan Hoffman
(74) *Attorney, Agent, or Firm* — Harness, Dickey & Pierce, P.L.C.

(57) ABSTRACT

Provided is a gastritis and gastric ulcer-treating agent, which is prepared and developed by processing solar salt and bamboo tree into heat-treated purple salt, in which the heat-treated salt, which is prepared by firstly heat-treating mineral rich solar salt and bamboo tree at a high temperature, that is, 1,100° C. or more; and two or more time repeating the heat-treating of the first heat-treated salt and bamboo tree under the above-described conditions, includes a large amount of hydrogen sulfide-producing material and has a purple color, and when the heat-treated salt is used along with aspirin, the heat-treated salt has an excellent effect on preventing stomach damage, thereby significantly reducing bleeding, ulcer, and the damage of mucous membrane, induced by aspirin.

8 Claims, 5 Drawing Sheets

REMEDY FOR GASTRITIS AND GASTRIC ULCER

CROSS-REFERENCE TO RELATED APPLICATIONS

This application is a continuation of U.S. patent application Ser. No. 14/649,753, filed Jun. 4, 2015, now abandoned, which is the national phase application of PCT Application No. PCT/KR2011/009614, filed on 14 Dec. 2011, which claims benefit of Korean Patent Application 10-2011-0050650, filed on 27 May 2011. The entire disclosure of the application identified in this paragraph is incorporated herein by reference.

TECHNICAL FIELD

The present invention relates to a gastritis and gastric ulcer-treating agent, and particularly, a gastritis and gastric ulcer-treating agent, which includes, as an active ingredient, heat-treated purple salt having a preventive effect of gastric damage, such as gastric hemorrhage, gastritis and gastric ulcer.

BACKGROUND

It is known that gastritis and gastric ulcer are stomach and intestines diseases caused by the damage of the gastric mucous membrane due to various internal and external aggressive factors, and are a high frequency of disease around the world. The stomach and intestines diseases occur by psychological stress, hyperacidity, increased gastrointestinal motility, and *Helicobacter pylori* infection and symptom thereof may be various types, such as, bleeding, inflammation, an ulcer, and destruction of mucosa, in addition to general pains. Especially, it is known that gastric ulcer has a high affinity with *Helicobacter pylori* infection, and in developing countries as well as advanced countries and Korea, 90% or more of adults are infected by *Helicobacter pylori*. In addition, it is known that nonsteroidal anti-inflammatory drugs (NSAIDs) such as aspirin and indomethacin lead to stomach damage, such as, bleeding, inflammation, and an ulcer by directly stimulating the gastric mucous membrane through selectively inhibiting the production of cyclooxygenase-2, which makes local blood circulation smoothly.

In order to treat the gastric damage, such as gastric ulcer, a hydrogen ion pump inhibitor that blocks acid secretion from the cells of stomach wall, gastric antiacids, the receptor blocker of histamine that catalyzes acid secretion, prostaglandin (PG) that is a gastric mucous membrane-reinforcing agent and a derivative thereof, antibiotics that inhibit the growth and development of *Helicobacter pylori*, and the like are being used.

The various gastric damage-treating or preventing agents described above lead to side effects and develop a tolerance when taken for long term. Therefore, efforts to develop a preventing or treating agent having excellent gastric treating effect from natural substances including food materials are actively proceeding. In other words, the discovery and development of natural substances having a gastric damage-preventing effect, which has no side effects when taken and no problems about tolerance or stability even when taken for a long period of time, are urgently needed.

Meanwhile, it is known that endogenous substances for protecting a body from gastric damage are prostaglandin (PG), an epidermal growth factor, a fibroblast growth factor, nitric oxide (NO), and the like. Recently, it is known that hydrogen sulfide exhibits toxicity in the case of an excess of quantity in a body, and is a signaling molecule of endogenous gas such as NO and CO (Sen N and Snyder S H, Trends in Neurosciences, 33, p. 493 to 502, 2010). It is confirmed that hydrogen sulfide is concerned in various biological activities, such as, vasodilatation, intercellular signaling, and anti-inflammatory activity (Benavides G A, et al., PNAS, 104, p. 17977 to 17982, 2007; Chen Y W, et al., Journal of Surgical Research, 164, P. e305 to e313, 2010). Especially, it is confirmed from an animal experiment that nonsteroidal anti-inflammatory drugs decreases the production of hydrogen sulfide in a body, but the food materials or drugs inducing the production of hydrogen sulfide decreases the gastric damage induced by the nonsteroidal anti-inflammatory drugs (Medeiros J V R, et al., The Journal of Pharmacology and Experimental Therapeutics, 330, p. 764 to 770, 2009). Especially, it is known that hydrogen sulfide inhibits adherence of white blood cells on the vascular endothelial along with nitric oxide and has a pain-blocking effect (Zanardo R C, et al., FASEB J, 20, 2118, 2006). Especially, it has been reported that garlic among food materials includes a larger amount of sulfur, and when taken the garlic, the production of hydrogen sulfide is increased in a body, an oxidative damage is decreased, and the effect on preventing cardiovascular disorders is exhibited (Benavides G A, et al., PNAS, 104, p. 17977 to 17982, 2007). Therefore, the food materials such as garlic that may help the production of hydrogen sulfide in a body may be an excellent health functional material.

Meanwhile, salt that is used as a seasoning agent making taste in our daily lives is mainly composed of sodium chloride (NaCl), which is physiologically a necessity for a person. In detail, sodium chloride controls the osmotic pressure of body fluid in a body, maintains acid-base balance in body fluid as a buffer substance, and forms alkaline digestive fluid in bile, pancreatic juice, or intestinal juice, and chlorine that is another constituent of sodium chloride forms gastric juice. As described above, the sodium chloride has the action that is closely involved in the biological activity and life conservation of animals, and thus, when the salt intake is low, in the case of the short time, the secretion of digestive fluid is lack, thereby occurring decrease of appetite and in the case of the long time, generalized weakness, tiredness, weariness, and internal malaise occur. When the loss of salt is sharply generated in a body, the clear loss of physical and psychological functions, such as dizziness, self-renunciation, and clouding of consciousness occurs.

However, it is known that when salt that is taken every day is oversupplied, blood pressure is increased and insulin signaling is influenced, thereby inducing insulin resistance. Especially, it is confirmed that sodium chloride that is a main component of salt is a direct cause substance leading hypertension and diabetes. For this reason, WHO/ISH recommends 5 g or less as adult daily intake of salt and Japanese Society of Hypertension recommends 7 g or less as adult daily intake of salt at 2000.

Salt that is intake may be largely classified into halite, white salt, refined salt, and solar salt, and it is known that the mineral contents in a salt are different depending on the different kinds of salts. In other words, halite and refined salt that are mainly intake around the world include 99% or more of sodium chloride content, but there are almost no mineral components, such as, K, Ca, and Mg. However, it is reported that mudflat solar salt that is produced in Korea includes 85% of sodium chloride content, but a large amount of mineral components, such as, K, Ca, and Mg (Kang Duck, Lee, et al., 2008, Symposium and regular general meeting of Korean Journal of Food Science and Technology, p. 282, Korean Journal of Food Science and Technology, Gwang Ju, 2008, 6, 18 to 20).

TABLE 1

| Salt | Mineral content (mg/kg) | | | | | | | |
|---|---|---|---|---|---|---|---|---|
| | K | Mg | Ca | Sr | Fe | Mn | Zn | Cu |
| Mudflat solar salt | 2494 | 8190 | 1459 | 98.6 | 12.5 | 3 | 0.8 | 1.3 |
| Refined salt | 1,823 | 364.8 | 126 | 15.3 | 14.9 | 1.9 | — | 1.5 |
| Reagent grade salt | ≤50 | ≤5 | ≤2 | ≤5 | ≤1 | ≤5 | ≤5 | ≤5 |

Especially, the mineral components, such as, K, Ca, and Mg, inhibit the rise of blood pressure and are positively correlated with insulin signaling. It is reported that K increases the production of NO, thereby relaxing endothelial blood vessel, and Ca influences the contraction-relaxation of muscle and blood vessel, and relaxes the blood vessel of hypertensive patient, thereby decreasing blood pressure (Franzoni F, et al., 2005. Biomedicine & Pharmacotherapy 59, p. 25 to 29, 2005; Wu X, et al., Cardiovascular Research, 40, 364 to 374, 1998). In addition, Mg increases the production of NO and also influences blood pressure by changing the structure of blood vessel (Sontia B, et al., Arichives of Biochemistry & Biophysics, 458, p. 33 to 39, 2007). Ogihara, et al. (Life Sciences, 73, p. 509 to 523, 2003; Hypertension, 40, p. 83 to 88, 2002) reported that the expression of glucose transporter-4 (GLUT4) was inhibited in salt-sensitive rat taken only in NaCl, thereby inhibiting insulin signaling, but the function of insulin signaling factor was normally performed in the salt-sensitive rat supplied with high concentration of K.

Recently, it has been reported that as compared with the salt without minerals, the mudflat solar salt inhibits the rise of blood pressure and also inhibits insulin receptor substrate-1 serine phosphorylation enzyme that is a negative control factor for insulin signaling. In addition, the mudflat solar salt increases glucose uptake in fat or muscle tissues, thereby decreasing insulin resistance (Ekkapon L, et al., 2008 14th World Congress of Food Science & Technology, TS25 to 37, Shanghai, China, Oct. 19, 2008 to 23; Lee KD, et al., 2008 14thWorld Congress of Food Science & Technology, TS25 to 83, Shanghai, China, Oct. 19, 2008 to 23). Therefore, it suggested that health effect of salt is different according to the amount of intake and also kinds of salt. It is considered that mudflat solar salt includes a large amount of mineral contents, and thus, is good for health.

Heat-treated salt (bamboo salt and the like) is prepared by burning or melting mudflat solar salt with bamboo, and is uniquely produced only in Korea. From ancient times, it is widely used for treating inflammation, diabetes, and the like, and recently, by scientists, it has been confirmed that there are various biological activities, such as, antioxidant activity, anti-inflammation, anti-virus, and anti-cancer, of the heat-treated salt (Gao T C, et al., 9th International Symposium, pp. 1345 to 1347, Beijing, China, 2009; Shin H Y, et al., immunophamacol immunotoxicol, 25, p. 377 to 384, 2003; Yang Ji Sun, et al., The Korean Society of Applied Pharmacology, 7, 178 to 184, 1999). In addition, it has been reported that even when bamboo salt is injected to a rat for 4 weeks, there are no anti-acid effects or inhibition effects of gastric acid secretions, and thereby, the intake of bamboo salt does not have an anti-gastric ulcer effect (Kim Seung Hee, et al., The Korean Society of Food Hygiene and Safety, 13, 1998). However, Hur, et al. (The Pharmaceutical Society of Korea, 45, 258, 2001) reported that when garlic and bamboo salt are injected into the rat induced by alcohol-nonsteroidal anti-inflammatory drug (salicylic acid), anti-gastric ulcer effect is exhibited.

The difference of anti-gastric ulcer effects of bamboo salt as described above may be generated due to the different kinds of bamboo salts that are used for the experiments. The bamboo salt being sold in the market may be gray bamboo salt, purple bamboo salt, and life bamboo salt, and there are various types of bamboo salts according to manufacturing companies. It suggested that bamboo salt exhibits anti-gastric ulcer effect, but it is confirmed that it is very difficult to find bamboo salt having excellent anti-gastric ulcer effect from the commercial available bamboo salts.

In addition, in order to prepare bamboo salt having excellent anti-gastric ulcer effect, it is determined that the method for preparing the bamboo salt is very important, but yet very few academic studies therefor have been done.

In order to increase availability of mineral rich mudflat solar salt that is mostly produced in Korea and to find natural materials having a stomach damage-preventing effect, which has no problem about stability even when is used for a long period of time, the development of heat-treated salt is being demanded, in which the heat-treated salt exhibits a preventing effect of stomach damage, such as, bleeding, inflammation, ulcer, and destruction of mucosa by treating the solar salt through various heat treatment processing methods.

The purple bamboo salt having a stomach damage-preventing effect to be prepared in the present invention was conventionally produced under the name of purple bamboo salt, and the conventional purple bamboo salt was prepared by passing the bamboo salt preparing process of eight-burning, and finally, burning it at a high temperature using a pine tree as a fuel in order to make the purple bamboo salt. This processes required many processes, long times, and a large amount of bamboo tree materials, and thus, the cost of fuel and personnel expenses are increased, thereby increasing the manufacturing cost, and also, the production amount of purple bamboo salt are irregular and it is difficult to perform the bulk production thereof. In addition, there are no studies exhibiting whether or not the conventional purple bamboo salt produced as described above has a stomach damage-preventing effect to be obtained in the present invention.

SUMMARY

Technical Problem

The inventors of the present invention conducted a thorough investigation with regard to the problems described above, and the as a result, the inventors found that the heat-treated salt, which is prepared by adding mineral rich solar salt produced in southwest seashore, Korea and a biennial bamboo tree or more in a ceramic container; firstly heat-treating the ceramic container at about 1,100° C. or more; mixing first heat-treated salt and bamboo tree again; and then, repeating the heat treatment twice or more, exhibits a purple color and has a large amount of the material capable of producing hydrogen sulfide that is known as an endogenous gas signaling material in a body. In addition, the inventors found that in the case of using the heat-treated salt along with aspirin, the heat-treated salt exhibits a stomach damage-preventing effect, thereby significantly decreasing stomach damage, such as, gastric hemorrhage, inflammation, ulcer, and destruction of mucosa, which may be caused by aspirin.

An object of the present invention is to provide purple heat-treated salt as a gastritis and gastric ulcer-treating agent, which includes a large amount of material producing hydrogen sulfide and does not have side effects in a body even in the case of daily ingestion.

Technical Solution

The gastritis and gastric ulcer-treating agent according to the present invention includes purple bamboo salt including a hydrogen sulfide-producing material as an active ingredient.

The hydrogen sulfide-producing material according to the present invention produces 1,066±13 μg of hydrogen sulfide with respect to 1 g of purple bamboo salt.

Advantageous Effects

When the purple bamboo salt that is a gastritis and gastric ulcer-treating agent according to the present invention is taken, there is very effective effect on preventing or improving stomach damage, such as, gastric hemorrhage, inflammation, ulcer, and the destruction of mucosa, which may be induced by the nonsteroidal anti-inflammatory drugs, such as, aspirin.

In addition, the mudflat solar salt used in the present invention includes an abundance of minerals, and thus, has an effect on decreasing oxidative damage, thereby being the gastritis and gastric ulcer-treating agent having the good effectiveness for stomach-related diseases as compared with any other salts.

The purple bamboo salt that is a gastritis and gastric ulcer-treating agent obtained by the present invention does not have side effects and stability problem unlike the conventional gastric ulcer-treating agents, and since the mudflat solar salt produced in southwest seashore, Korea is used, it is financially lucrative, and thus, has a great effect, industrially.

DETAILED DESCRIPTION

Figure 1:
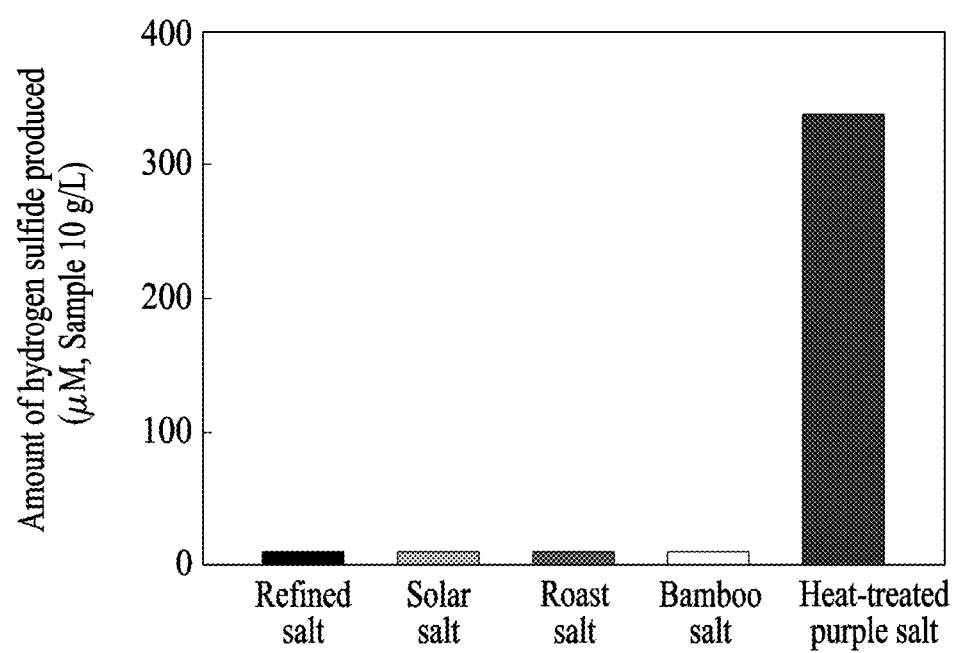
FIG. 1 is a graph illustrating the hydrogen sulfide production amounts in refined salt, solar salt, the roast salt prepared by heat-treating only solar salt once, the bamboo salt prepared by heat-treating solar salt and bamboo tree once, and the heat-treated purple salt prepared by repeatedly heat-treating solar salt and bamboo tree, according to an embodiment of the present invention.

Hereinafter, the present invention will be described in more detail.

The solar salt used in the present invention means a salt prepared by vaporizing water from seawater in a salt pond through wind and sunshine, and the solar salt may include 75 to 95 wt % of the sodium chloride content, 0.1 to 0.3 wt % of the calcium content, 0.2 to 0.6 wt % of the potassium content, and 0.8 to 2.0 wt % of the magnesium content, with respect to the total salt weight, and may further include manganese (Mn), iron (Fe), copper (Cu), zinc (Zn), and strontium (Sr).

In addition, the bamboo tree used in the present invention a generic term for evergreen perennial plants that belong to a monocotyledon poales graminae bamboo subfamily, and may be preferably two-year old to four-year old of normality degree of the bamboo tree. The sap in the bamboo tree is insufficient at a week or so after cutting, and thus, it is preferable to use the bamboo tree immediately after cutting. For example, the bamboo tree being two-year old to four-year old of normality degree may be cut, and then, may be cut and used in a cylindrical form, or may be crushed and then may be used in a chip form.

The purple bamboo salt prepared according to the present invention is prepared by the following process.

The method for preparing the purple bamboo salt includes adding mudflat solar salt and cutting bamboo chips into a ceramic container; heating the ceramic container at 1,000 to 1,200° C. for 50 to 90 minutes; sealing the heated ceramic container and then leaving the container until it is cooled to be room temperature, for example, about 15° C. to 25° C.; pulverizing the salt taken out from the cooled ceramic container; and repeating the heating and cooling to be room temperature two to five times by the same method as described above after further adding the bamboo chips to the pulverized salt, in which the mudflat solar salt and cutting bamboo chips are added in the amounts of 50 to 80 wt % of the mudflat solar salt and 20 to 50 wt % of the bamboo tree, and the method includes repeating the heating and cooling to be room temperature eight times by the same method as described above after further adding the bamboo chips to the pulverized salt.

A process for preparing the purple bamboo salt that is a gastritis and gastric ulcer-treating agent will be described in more detail as follows.

For the step of heating the mixture of the solar salt and bamboo tree, the mixture of the solar salt and bamboo tree are added to a sealable ceramic container; and then, the heat is raised by gas until the container is to be 1,000 to 1,200° C., and preferably 1,100° C.; and then, the heat treatment is performed for 30 minutes to 2 hours, and preferably 1 hour to 1 hour and a half. When the solar salt is heated at a high temperature as described above, the purple bamboo salt having antioxidative activity is produced.

When the temperature is less than the above temperature range, the purple bamboo salt is not produced. However, it is not necessary to heat at 1,200° C. or higher, excessively. For the heating time, it is difficult to produce a large amount of purple bamboo salt for less than the above heating time. It is possible to heat for the above heating time or more, but it is not preferable in terms of efficiency.

For the mixing ratio of the solar salt and bamboo tree, a method for mixing them in 50:50 to 80:20, and preferably 60:40 to 75:25 may be performed on the basis of the weight ratio of the solar salt and bamboo tree. It is possible to add the bamboo chips by the maximum 50 wt %, but in order to increase the effectiveness of bamboo salt, it is not necessary to add too many chips. When too many bamboo trees are added, a large amount of ashes are generated, and thus, the ashes are mixed with the salt. Therefore, it is not preferable.

Even when the amount of bamboo tree is about 20 wt % at the lowest, there are no problems for producing the purple bamboo salt. When the bamboo tree is heated with the salt, the entire bamboo tree is burned and then is integrated into the salt, thereby remaining only a lump of the salts. A part of ashes or some bamboo trees may be remained, but after removing them, the lump of the salts are ground, and then, are subjected to the following processes.

The bamboo tree in the above-described ratio is added to the heat-treated salt obtained by the first heat treatment in the sealable ceramic container; the sealable ceramic container is subjected to the heat treatment under the above-described heat treatment conditions; the sealable ceramic container is sealed; and then, the container is left to be cooled to room temperature, for example, about 15° C. to 25° C. The number of the heat treatments after mixing the second heat-treated salt and bamboo tree again may be two or five time and more preferably three to four times. When the salt is subjected to the above-described heat treatment process, it is possible to produce the heat-treated purple salt having a large amount of hydrogen sulfide-producing material.

The heat treatments are performed at least two times by the above-described method, and thus, it is possible to obtain the purple salt of good quality.

Hereinafter, the preferred Examples of the present invention will be described. However, the following Examples are only for illustrating the present invention, and the present invention is not limited to the following Examples.

EXAMPLES

Example 1

Preparation of heat-treated purple salt.

The mudflat solar salt used in the present invention was produced in Sinan-gun, Jeollanam-do, Korea, and refined salt without minerals was purchased in the market, and then used. In order to prepare heat-treated purple salt having a large amount of materials capable of producing hydrogen sulfide, which have an effect on preventing stomach damage, two-year or more old bamboo tree that was used as a minor ingredient was purchased, and then, used.

Mineral rich mudflat solar salt and bamboo tree cut in a chip form were added in a ceramic container, and then, the container was subjected to a heat treatment for 1 hour after the temperature of the container is increased at 1,100° C. using gas.

In other words, the heat treatment was performed at 1,100° C. for 1 hour after 70 wt % of the mudflat solar salt and 30 wt % of bamboo tree were mixed in the ceramic container. In the state of being completely burned, the bamboo tree was completely integrated into the salt, thereby forming a lump of the salt. The lump of the salt was ground to make the salt, and then, 70 wt % of the heat-treated salt thus obtained and 30 wt % of the new bamboo chip were mixed and added in a sealable ceramic container. Since then, the sealable ceramic container was subjected to the heat treatment under the same conditions as the first heat treatment described above; then, was sealed; and then, was left until the container was cooled to be room temperature.

The above-described processes were repeated two to five time to prepare heat-treated purple salt.

In addition, the roast salt prepared by heating only solar salt and the bamboo salt prepared by heating the mixture of solar salt and bamboo tree were prepared by performing the heat treatment under the same conditions as described above, that is, at 1,100° C. for 1 hour once.

The addition of the bamboo chips and heating processes may be performed up to nine time or more. However, in terms of time, cost, and productivity, it is preferable to perform them five or less time.

Example 2

Confirmation of content of hydrogen sulfide-producing material in heat-treated purple salt.

In the heat-treated purple salt prepared as described above, mudflat solar salt, bamboo salt, and refined salt, as an object, the contents of the hydrogen sulfide material were investigated. In other words, each of the samples (10.0 g) was dissolved in distilled water (1 L), and then, centrifuged for 2 minutes to remove insoluble materials in order to prepare a sample solution. The prepared sample solution (430 μL) was mixed with 50 μL of saline solution. 250 μL of 1% zinc acetate solution and 250 μL of distilled water were added thereto; 133 μL of the solution of 20 mM N,N-dimethyl-p-phenylendediamine sulfate dissolved in 7.2 M HCl solution and 133 μL of the solution 30 mM $FeCl_3$ dissolved in 1.2 M HCl solution were added thereto; and then, the mixture thus obtained was reacted at room temperature for 5 minutes. The absorbance of the reaction solution thus obtained was measured at 670 nm using a 96 well microplate reader. In addition, a standard curve was made using a standard material, NaHS (3.125 to 200 μM), and then, the content of hydrogen sulfide produced from the salt was obtained using the standard curve.

As illustrated in FIG. 1, there were no hydrogen sulfides in the refined salt without minerals, the mineral rich mudflat solar salt, the roast salt prepared by heating only solar salt once, and the bamboo salt prepared by heating the mixture of bamboo tree and solar salt once. Interestingly, the large amount of hydrogen sulfide was detected in the heat-treated purple salt according to the present invention. For this reason, it was confirmed that a large amount of materials capable of producing hydrogen sulfide was existed in the heat-treated purple salt according to the present invention.

In other words, it could be confirmed that the amount of hydrogen sulfide produced was 1,066±13 μg in 1 g part by weight of the heat-treated purple salt according to the present invention.

Form the above result, it can be confirmed that the heat-treated purple salt according to the present invention includes a large amount of compounds producing hydrogen sulfide, which has various biological activities, such as, vasodilatation, cell metabolism decrease, anti-inflammation, and anti-gastric ulcer in a body, and thereby, it can be expected that the heat-treated purple salt according to the present invention can be used as a functional heat-treated salt having a large amount of hydrogen sulfide-inducing material.

Example 3

Confirmation of effect of heat-treated purple salt on preventing stomach damage and hydrogen sulfide-producing material in the rat having stomach damage induced by aspirin.

The effect of the heat-treated salt prepared in Example 1 on preventing stomach damage was tested.

In order to measure an effect on preventing stomach damage, five-week Wistar rats were purchased from Central Lab. Animal Inc., Seoul, Korea. A breeding room was set to be 20° C. of the temperature, 50 to 60% of relative humidity, and 12 hours of lighting cycle, and water and food were set to be freely taken. The test animals were accommodated for 2 weeks using a general feed prepared on the basis of AlN-93G, and then, the weights of the animals were measured to divide them into each of test groups (n=8). Since then, the test groups were a normal group (Con) injected with distilled water only, a control group (NaCl) injected with pure sodium chloride (NaCl, 0.167 g/kg BW) that was a main ingredient of salt only, and a heat-treated salt-treating group injected with heat-treated purple salt (0.167 g/kg BW), in which each of sample solutions was orally injected along with aspirin (50 mg/kg BW) once every day for 5 weeks. In addition, glibenclamide (10 mg/kg BW) solution inhibiting $K_{ATP}$ channel dissolved in 0.01 N NaOH including 4% glucose was abdominally injected 1 hour before orally injecting aspirin (50 mg/kg BW) and heat-treated salt (0.167 g/kg BW), and performed once every day for 5 weeks. The respective treating groups were fasted for 24 hours before sacrificing; sacrificed; and then, the stomach was removed. The removed stomach was cut along greater curvature of stomach; opened; and then, washed with 13 mL of saline solution; and the cut part was observed with an optical microscope (Olympus).

Figure 2:
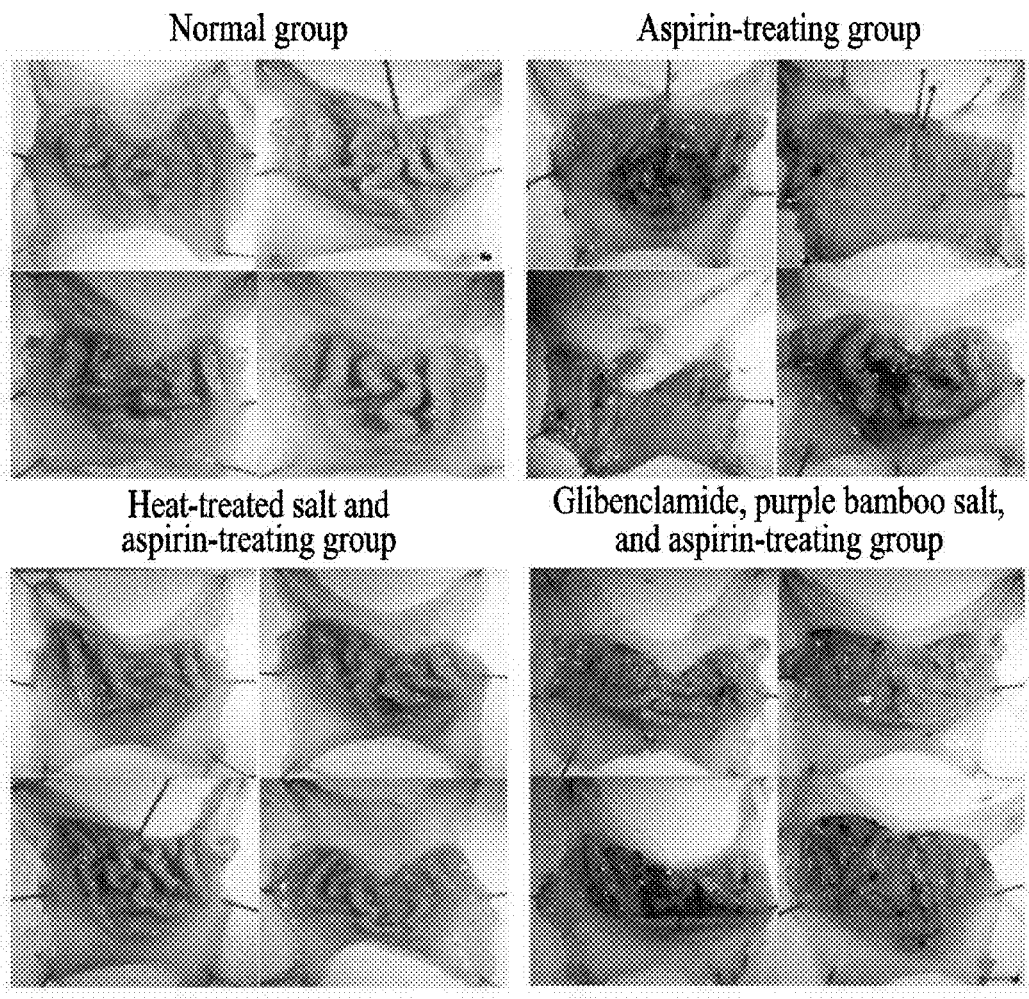
FIG. 2 is photographs illustrating the effect of the heat-treated purple salt according to an embodiment of the present invention on preventing stomach damage, such as, bleeding, inflammation, and ulcer in Wistar rats.

As illustrated in FIG. 2, it could be confirmed that the group treated with aspirin exhibited severe damage along with gastric hemorrhage, and also, there were no mucosa membrane or there were severe damaged mucosa membranes, if any.

Like a normal group, the group treated with the heat-treated purple salt according to the present invention did not exhibit stomach damage, such as, bleeding and inflammation. As an effect on preventing stomach damage through the activation of $K_{ATP}$ channel, hydrogen sulfide is proven to be ineffective in preventing stomach damage by treating glibenclamide that is a $K_{ATP}$ channel antagonist (Mederios J V R, Pharmacology and Experimental Therapeutics, 330, 764 to 770, 2009).

As suggested in Example 2, it was confirmed that hydrogen sulfide was produced from the heat-treated purple salt, and thereby, it highly suggested the potential of hydrogen sulfide for contributing an effect of the heat-treated purple salt according to the present invention on preventing stomach damage. In other words, for the present invention, when there are no effects on preventing stomach damage induced by aspirin at the time of treating glibenclamide that is a $K_{ATP}$ channel antagonist and also the heat-treated purple salt, it can be considered that hydrogen sulfide produced from the heat-treated purple salt exhibits an effect on preventing stomach damage induced by aspirin through the activation of $K_{ATP}$ channel.

Figure 3:
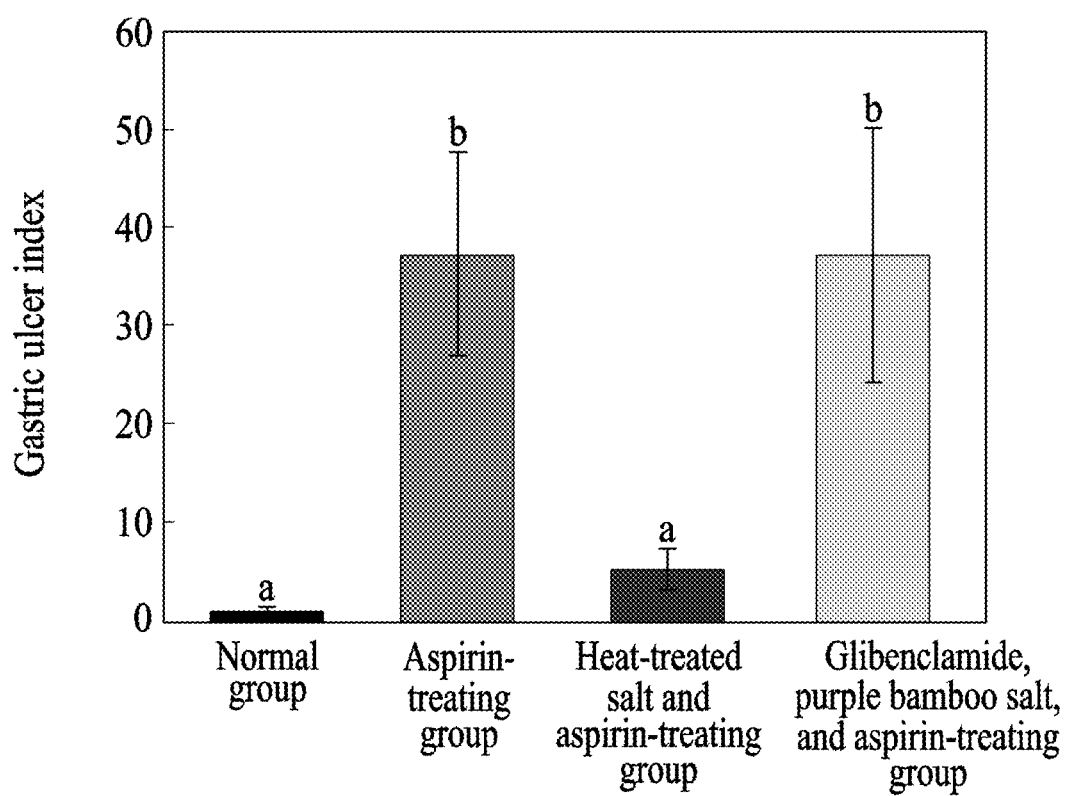
FIG. 3 is a graph illustrating gastric ulcer index of the heat-treated purple salt having an effect on preventing gastric ulcer, according to an embodiment of the present invention.

As illustrated in FIG. 3, from the results of the oral injection of the heat-treated purple salt and glibenclamide that is a $K_{ATP}$ channel antagonist, it can be confirmed that there are no effects on preventing stomach damage induced by aspirin. Therefore, it is considered that hydrogen sulfide produced from the heat-treated purple salt suppresses stomach damage induced by aspirin.

Therefore, as the result of Example 2, it can be confirmed from an animal experiment that the heat-treated purple salt includes a large amount of material capable of producing hydrogen sulfide.

Example 4

Effect of heat-treated purple salt on suppressing gastric ulcer in rat having stomach damage induced by aspirin.

An effect of the heat-treated purple salt obtained in Example 2 on suppressing gastric ulcer was measured. The effect on suppressing gastric ulcer was expressed as a gastric ulcer index by measuring the degree of gastric ulcer [1, gastric hemorrhage region; 2=very small damaged region; 3, 1 to 5 small damaged regions of 2 mm or less; 4, 5 or more small damaged regions of 2 mm or less; 5, 1 to 3 large damaged regions of 2 mm or more; 6, 3 or more large damaged regions of 2 mm or more] according to the method suggested by Dekanski, et al., (Br J Pharmacol, 55, 387 to 392, 1975) using an optical microscope (Olympus).

As illustrated in FIG. 3, it can be confirmed that the gastric ulcer index of aspirin-treating group is very high, that is, 37.3±10.4. However, it can be also confirmed that the gastric ulcer index of the group treated with the heat-treated purple salt is 5.1±2.1, that is very low level as compared with the aspirin-treating group and almost the same as that of the normal group. In addition, the gastric ulcer index of the group treated with the heat-treated purple salt and glibenclamide that is a $K_{ATP}$ channel antagonist is almost the same as that of the aspirin-treating group. The reason is considered that hydrogen sulfide produced from the heat-treated purple salt exhibits an effect on suppressing gastric ulcer induced by aspirin. Therefore, it can be confirmed that the effect of the heat-treated purple salt according to the present invention on suppressing gastric ulcer is about 75% or more on the supposition that the gastric ulcer index of the aspirin-treating group is 100%.

Example 5

Effect of heat-treated purple salt on suppressing the damage of gastric mucous membrane in rat having stomach damage induced by aspirin.

A degree of the damage of gastric mucous membrane of the heat-treated purple salt obtained in Example 2 was measured by measuring a stomach thickness. In more detail, the removed stomach was fixed in 0.1 M PBS buffer solution dissolved with 2% glutaraldhyde and 2% paraformaldehyde for 12 hours. Each of the fixed samples was dehydrated with ethanol and xylene, and then, embedded with parafilm and wax. The embedded samples were cut in a size of 3.0 µm, were stained with hematoxylin and eosin, and then, were observed with an optical microscope (Olympus, ×20). Since then, the stomach thicknesses were measured using an ocular micrometer.

Figure 4:
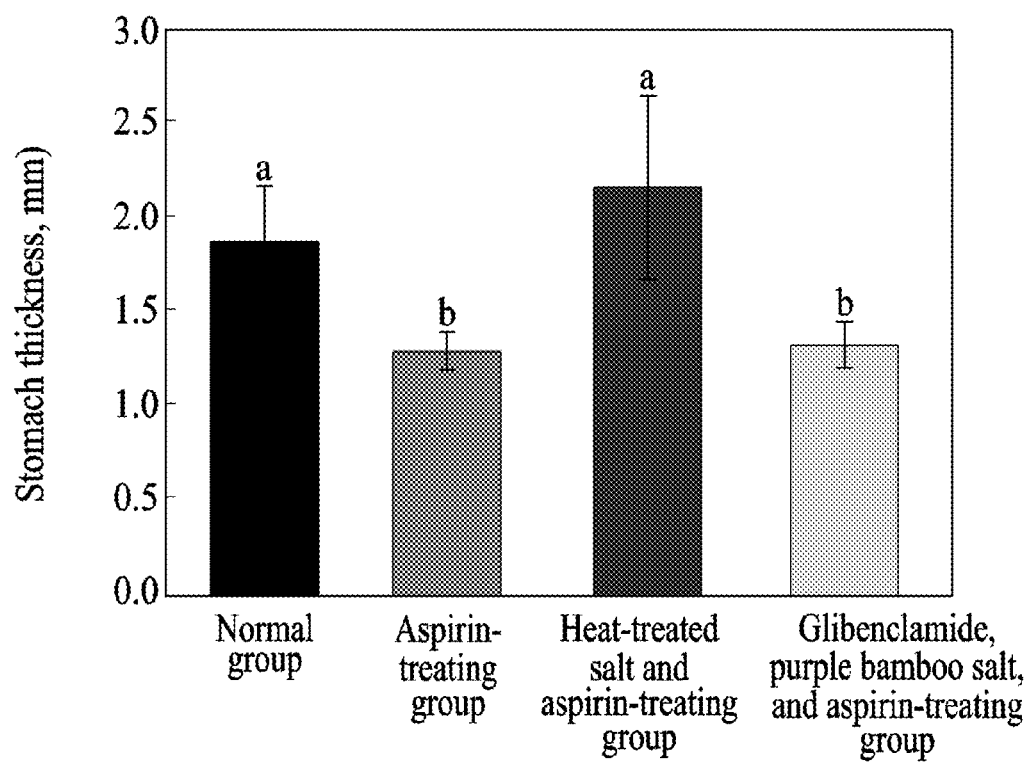
FIG. 4 is a graph illustrating stomach thickness by the heat-treated purple salt having an effect on preventing gastric ulcer, according to an embodiment of the present invention.
Figure 5:
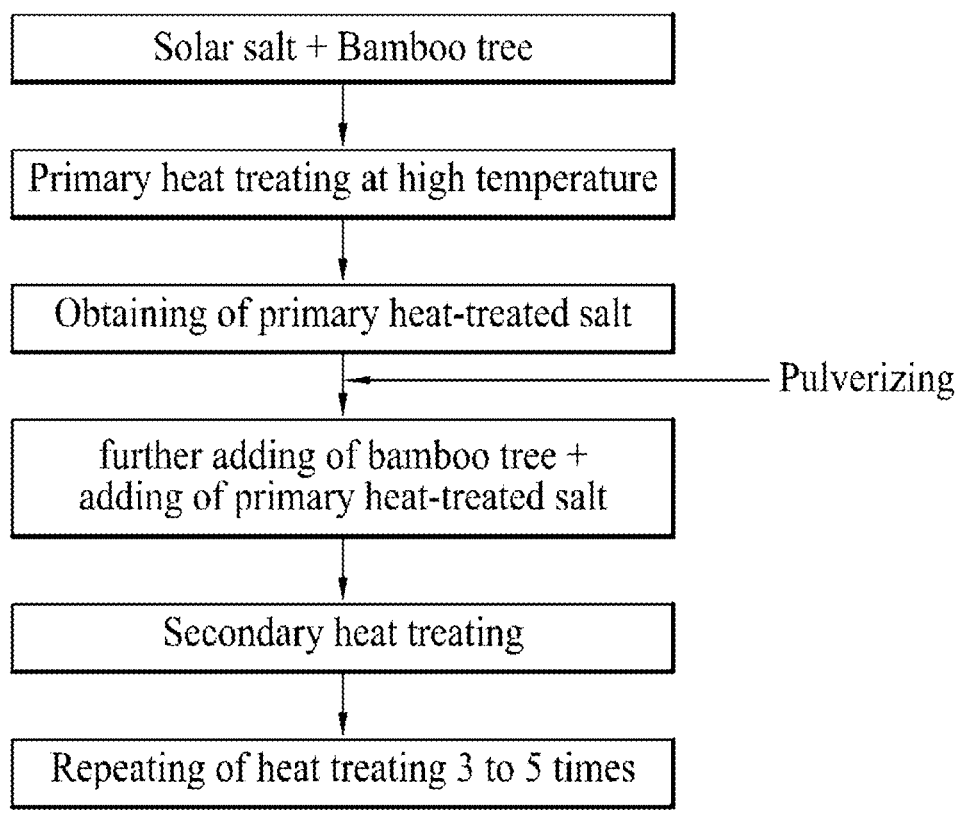
FIG. 5 is a diagram illustrating a process for preparing purple bamboo salt that is a gastritis and gastric ulcer-treating agent.

As illustrated in FIG. 4, it can be confirmed that the stomach thickness of the group treated with the heat-treated purple salt is 2.15±0.5, that is slightly thinker than that of the normal group (1.86±0.3), but there is no significant difference between them. However, it can be confirmed that the stomach thickness of the aspirin-treating group becomes very thin as compared with the normal group or the group treated with the heat-treated purple group. In addition, the stomach thickness of the group treated with glibenclamide that is a $K_{ATP}$ channel antagonist and also the heat-treated purple salt is almost the same as that of the aspirin-treating group. From the above-described result, it can be considered that hydrogen sulfide produced from the heat-treated purple salt suppresses the damage of gastric mucous membrane induced by aspirin through the activation of $K_{ATP}$ channel. Therefore, it can be confirmed that the heat-treated purple salt exhibits an effect on preventing stomach damage, such as, gastric ulcer and the damage of gastric mucous membrane, induced by aspirin.

From the above-described results, it can be confirmed that the heat-treated purple salt according to the present invention includes a large amount of hydrogen sulfide-producing material, and thus, exhibits an effect on preventing stomach damage, such as, bleeding, ulcer, and the damage of mucous membrane, induced by aspirin, and thereby, particularly, it can be expected that hydrogen sulfide produced from the heat-treated purple salt can prevent or improve stomach damage, such as, gastric ulcer and the damage of mucous membrane through the activation of $K_{ATP}$ channel. Therefore, it can be expected that the heat-treated purple salt according to the present invention is a functional heat-treated salt capable of producing a large amount of hydrogen sulfide, and can be effectively used as a gastritis and gastric ulcer-treating agent.

What is claimed is:

1. A method for treating gastritis or gastric ulcer comprising:
   administering to a subject in need thereof an effective amount of purple bamboo salt containing a mineral and a hydrogen sulfide-producing material,
   wherein the purple bamboo salt is prepared by a method comprising:
   adding mudflat solar salt and cut bamboo chips into a container, and heating the container at a temperature of 1,000 to 1,200° C.

2. The method of claim 1, wherein the hydrogen sulfide-producing material has 1,066 ±13 μg of an amount of hydrogen sulfide produced with respect to 1 g of the purple bamboo salt.

3. The method of claim 1, wherein the step of heating occurs for 50 to 90 minutes.

4. The method of claim 3, wherein the method further comprises sealing the heated container and leaving the container until it is cooled to a temperature of about 15° C. to about 25° C.

5. The method of claim 4, wherein the method further comprises:
   adding 50 to 80% by weight of mudflat solar salt and 20 to 50% by weight of cut bamboo chips, and
   repeating the steps of heating and cooling two to five times.

6. The method of claim 5, wherein the step of adding mudflat solar salt and cut bamboo chips comprises adding about 75% by weight of mudflat solar salt and about 25% by weight of cut bamboo chips.

7. The method of claim 6, wherein the step of heating the container comprises heating the container to about 1100° C.

8. The method of claim 4, wherein the step of repeating the steps of heating and cooling comprises repeating the steps of heating and cooling seven times.

* * * * *